United States Patent [19]

Scott

[11] Patent Number: 6,007,541
[45] Date of Patent: Dec. 28, 1999

[54] DUAL-BLADED RECIPROCATING BONE SAW

[75] Inventor: Tony D. Scott, Weatherford, Tex.

[73] Assignee: Midas Rex, L.P., Fort Worth, Tex.

[21] Appl. No.: 09/004,878

[22] Filed: Jan. 9, 1998

[51] Int. Cl.$^6$ .................................................. A61B 17/14
[52] U.S. Cl. .............................. 606/82; 606/177; 30/369
[58] Field of Search .................................. 606/82, 81, 80, 606/79, 83, 84, 85, 86, 87, 88, 89, 177; 30/369, 501, 503, 503.5; 74/25, 55, 56, 60

[56] References Cited

U.S. PATENT DOCUMENTS 5,359,809  11/1994  Spender .
5,427,188  6/1995   Fisher .
5,846,244  12/1998  Cripe ........................................ 606/82

*Primary Examiner*—Michael Buiz
*Assistant Examiner*—David O. Reip
*Attorney, Agent, or Firm*—Senniger, Powers, Leavitt & Roedel

[57] ABSTRACT

The invention relates to a handheld surgical power saw intended to be an integrated surgical tool or an attachment to a motorized surgical tool. The tool consists of two arms that reciprocate in opposite directions at all times. Attached to each arm is a set of cam followers and a saw blade. The arms are driven by a cam with outer surfaces that smoothly undulate between the two sets of cam followers.

22 Claims, 2 Drawing Sheets

DUAL-BLADED RECIPROCATING BONE SAW

TECHNICAL FIELD

The present invention relates in general to surgical instruments. In particular, the present invention relates to a surgical instrument used for the resection of bone and other tissue.

BACKGROUND ART

Surgical sawing tools for use in the resection of bone and tissue during surgical procedures are common. Inventions in the prior art utilize single blades, offset blades and chisels in a variety of configurations. Some utilize a reciprocating action while others use a lateral stroke. Inventions in the prior art also experience a number of problems. The single blade configuration will tend to bind up during a surgical procedure if the speed of the blade is diminished or the teeth of the blade catch on bone or tissue. Some of these designs utilize many gears and other moving parts which can be prone to fail. In addition, the rapid reciprocating action of these power tools can affect the precision of the instrument during surgery. What is needed is a smooth and efficient means for sawing that avoids binding and eliminates excessive moving parts that may fail.

DISCLOSURE OF INVENTION

A completely integrated surgical sawing tool contains a motor with a drive shaft. The rotary speed of the drive shaft is reduced through a gear box below which extends an output shaft. The output shaft also extends downward through an open cylindrical chassis. An undulated cam is attached to the shaft. Two rectangular slots are formed on opposite sides of the chassis. An arm slidingly reciprocates within each slot. The arms each ride upon a friction-reducing sleeve which is located between the arm and the chassis. The arms and chassis fit inside a friction-reducing cylindrical shell and the shell fits within an outer housing. Attached to each arm is a cam follower set. Each cam follower set comprises two cam followers which are spaced apart and secured to the inner surface of each arm with pins so that the cam followers may freely rotate. The arms and cam followers are located so that the outer edge of the cam extends between and in contact with each cam follower. When the output shaft rotates, the cam smoothly undulates between both cam follower sets thereby forcing the arms to slidingly reciprocate in opposite directions. The lower end of each arm has a mechanism for securing a saw blade. With the blades installed, the arms can slidingly reciprocate in opposite directions and be used for surgical sawing.

BEST MODE FOR CARRYING OUT THE INVENTION

Figure 1:
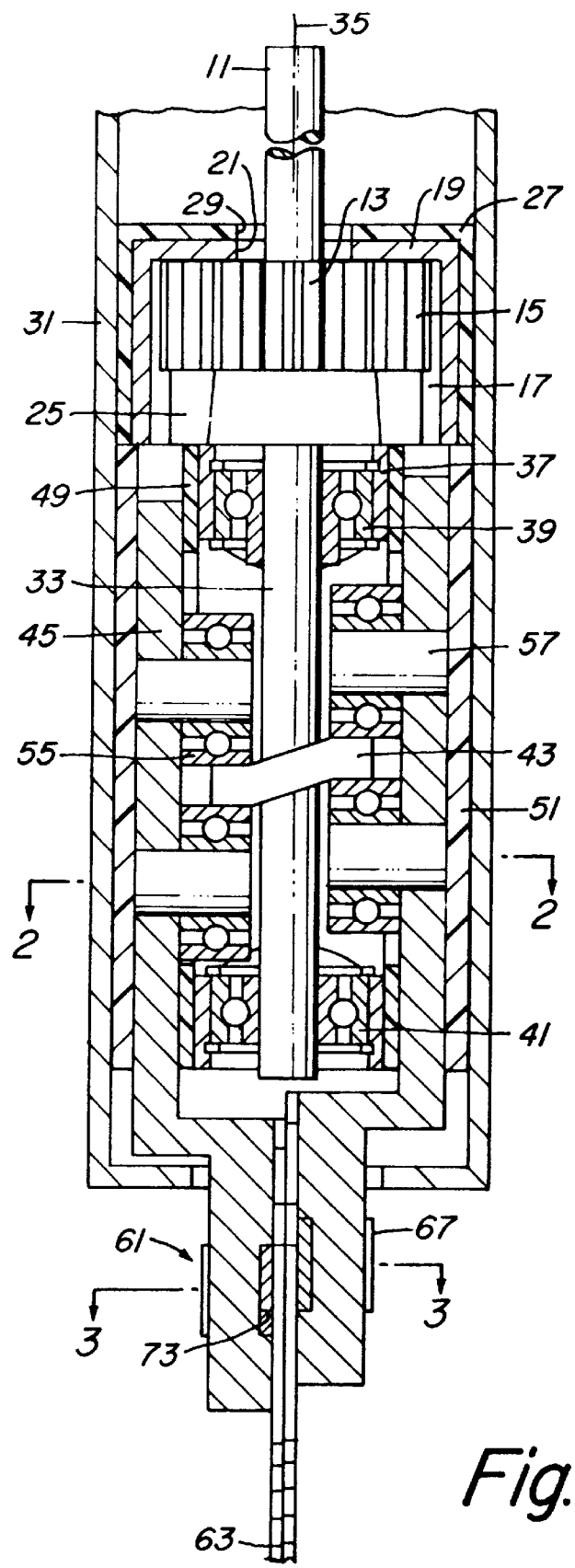
FIG. 1 is an elongated, axial cross-sectional view of a first example of a tool constructed in accordance with the invention.

FIG. 1 shows the components of one embodiment of a surgical sawing tool. The surgical sawing tool may be a releasable attachment to a motor (not shown) or coupled permanently to the motor. Motor drive shaft 11 is driven by a motor, preferably pneumatic, extends downward through holes 21 and 29 in upper housing 19 and cap 27, respectively, and is attached to pinion 13. When shaft 11 is rotated, planetary gears 15 orbit around pinion 13 and inside of annular gear 17. Annular gear 17 is integrally formed on the inside of upper housing 19. Upper housing 19 fits tightly inside of cap 27 which fits securely within an outer housing 31. Planetary gears 15 rotate on spindles 23 (not shown) which are integrally formed with backplate 25. Consequently, the rotation of planetary gears 15 rotate backplate 25. Backplate 25 is rigidly secured to an input shaft 33, which in turn rotates around central axis 35. Shaft 33 extends downward through and is secured to open cylindrical chassis 37 with bearings 39 and 41. An undulated cam 43 is integrally formed with shaft 33 near its longitudinal midpoint.

Figure 2:
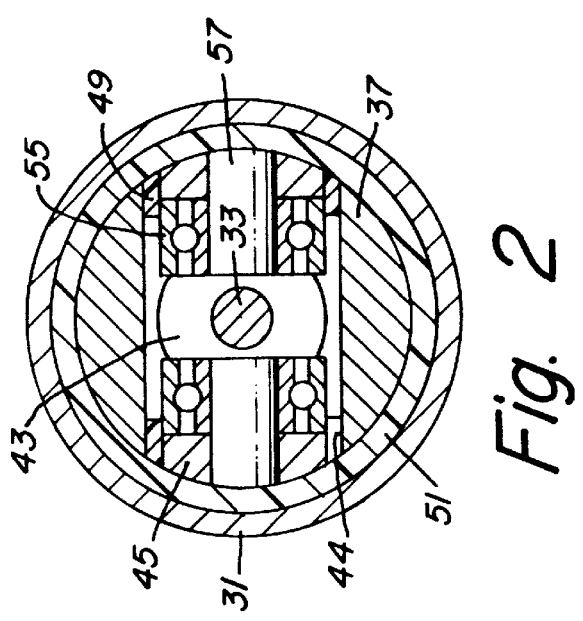
FIG. 2 is a transverse cross-sectional view of the tool of FIG. 1, taken along the line 2—2.

As shown in FIG. 2, two rectangular slot-like openings 44 are formed on opposing sides of chassis 37. Arms 45 slidingly reciprocate within slots 44. Arms 45 ride upon two thin, friction-reducing sleeves 49 which are located between arms 45 and chassis 37. Arms 45 and chassis 37 fit inside a thin, friction-reducing cylindrical shell 51. Shell 51 has the same outside diameter as that of cap 27 and also fits securely within outer housing 31.

Attached to each arm 45 is cam follower or bearing set 53. Each bearing set 53 comprises two cam followers or roller bearings 55 which are secured to the inner surface of arms 45 with pins 57 so that they may freely rotate.

A cam 43 is located between the arms. Cam 43 has upper and lower surfaces that are transverse to central axis 35. Each surface has peak and a valley. The peak on one side of cam 43 is 180 degrees out of phase from the peak on the other side of cam 43. Likewise, the valleys are also 180 degrees out of phase. Cam 43 also has an outer edge which is parallel to central axis 35 and represents a thickness of cam 43. Bearings 55 of bearing set 53 are spaced apart by a dimension approximately equal to that of the thickness of cam 43. Arms 45 and bearings 55 are positioned so that the outer edge of cam 43 extends between and in contact with each of the four bearings 55, but cam 43 is free of contact of arms 45. When shaft 33 rotates, cam 43 smoothly undulates between both bearing sets 53 thereby forcing arms 45 to slidingly reciprocate in opposite directions between sleeves 49 and shell 51 in slots 44 of chassis 37.

Figure 3:
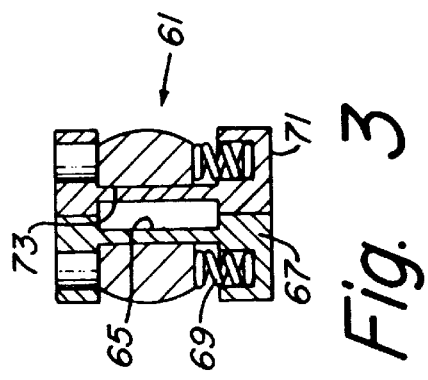
FIG. 3 is an enlarged partial cross-sectional view of the tool of FIG. 1, taken along the line 3—3, showing the blade retention mechanism without the blades in place.
Figure 4:
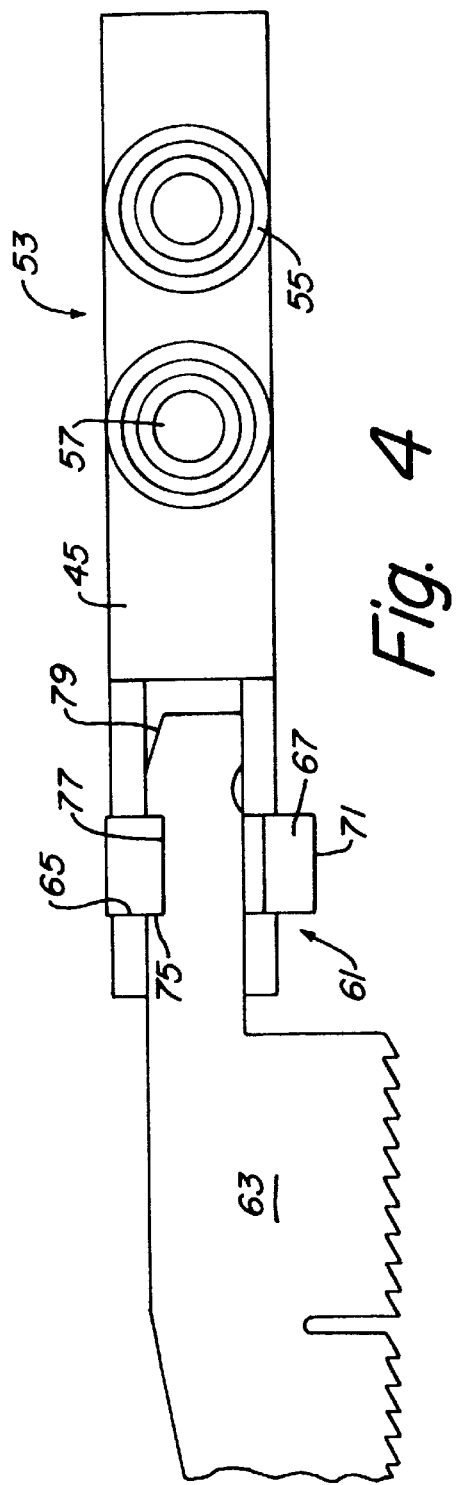
FIG. 4 is an enlarged side view of a single arm and saw blade.

As shown in FIGS. 3 and 4, a mechanism 61 for securing a saw blade 63 extends from the lower end of each arm 45. On the inner surface of mechanism 61 is a slot or groove 73 into which locking tab 67 is attached. Tab 67 is biased against mechanism 61 by spring 69. A slot or groove 65 of approximately the same width and thickness of blade 63 is formed in each mechanism 61. Notch 77 is formed in blade 63 and is approximately the same width as tab 67. The upper end 79 of blade 63 is tapered to facilitate entry into groove 65 of mechanism 61. When blade 63 is inserted into groove 65, the taper on upper end 79 forces lock 75 on tab 67 out of groove 65 until notch 77 is directly beneath lock 75. At that point spring 69 snaps tab 67 and lock 75 down into notch 77 and securely holds blade 63 in place. Blade 63 may be slidingly removed by simply depressing plunger end 71 of tab 67 so that lock 75 disengages notch 77. Blades 63 are in sliding contact with each other so that when they are installed in mechanisms 61, arms 45 can slidingly reciprocate in opposite directions and be used for surgical sawing.

In operation, the motor (not shown) rotates drive shaft 11, which in turn rotates shaft 33 at a slower speed due to pinion 13 and gears 15. Cam 43 rotates on shaft 33, engaging cam roller bearings 55 to alternately raise and lower arms 45. This causes blades 63 to reciprocate alternately with each other.

The invention has several advantages. Because the device can be an attachment to a conventional motorized surgical instrument, pre-existing rotary machines can be utilized without additional modification. The invention's dual-reciprocating blades combine exceptional sawing capacity with very smooth operation to allow surgeons to perform precise operations with minimal instrument vibration. Thrust created by downward movement of one blade is countered by thrust created by upward movement of the alternate blade. This design also minimizes the complexity of such devices and the number of moving parts required to accomplish its task, thereby increasing its reliability and longevity.

While the invention has been shown in only one of its forms, it should be apparent to those skilled in the art that it is not so limited, but is susceptible to various changes without departing from the scope of the invention.

I claim:

1. An apparatus for sawing during a surgical procedure comprising:
    an outer housing;
    a chassis with a longitudinal axis and mounted in the outer housing;
    a rotatably-driven input shaft extending axially into the housing;
    a pair of arms mounted to the chassis for axial reciprocal movement relative to the chassis;
    conversion means for converting the rotary motion of the input shaft into a reciprocating motion of each arm; and
    mounting means on a lower end of each of the arms for mounting a saw blade thereto for motion therewith.

2. The apparatus according to claim 1, further comprising a thin, friction-reducing insert separating each arm from the chassis and upon which each of the arms slide.

3. The apparatus according to claim 1, further comprising a thin, friction-reducing shell separating the arms and the chassis from the outer housing, each of the arms smoothly reciprocating between the shell and the chassis.

4. The apparatus according to claim 1, further comprising:
    a thin, friction-reducing insert separating each arm from the chassis and upon which each of the arms slide; and
    a thin, friction-reducing shell separating the arms and the chassis from the outer housing, each of the arms smoothly reciprocating between the shell and the chassis.

5. The apparatus according to claim 1, further comprising:
    a gear box coupled to the input shaft for reducing the rotational speed of the input shaft;
    an output shaft coupled to the gear box; and
    wherein the conversion means is coupled to the output shaft.

6. The apparatus according to claim 1 wherein the mounting means is adapted to position the saw blades in sliding contact with each other.

7. The apparatus according to claim 1, wherein each of the mounting means comprises:
    an axial slot on a lower end of each arm for receiving a saw blade; and
    a spring-loaded locking tab that locates in a transverse slot on the lower end of each arm, the tab adapted to engage a notch formed in the saw blade for securing the saw blade to the arm.

8. The apparatus according to claim 1, wherein the conversion means comprises a cylindrical cam having an annular cam surface, the cam being mounted on the shaft for rotation therewith.

9. The apparatus according to claim 1, wherein the reciprocating motions of the arms are synchronized 180 degrees out of phase with each other.

10. A surgical instrument for sawing comprising:
    an outer housing;
    a chassis with a longitudinal axis and mounted in the outer housing;
    a rotatably-driven shaft having a rotational axis and located in the chassis;
    a pair of arms mounted to the chassis for axial reciprocal movement relative to the chassis;
    mounting means on a lower end of each of the arms for mounting a saw blade thereto for motion therewith;
    a cylindrical cam having an annular cam surface with a peak 180 degrees from a valley, the cam being mounted on the shaft for rotation therewith; and
    at least two cam followers, each with a rotational axis, each of the cam followers rotatably mounted on an inner surface of the arms so that the axes of the cam followers are perpendicular to the axis of the shaft, each of the cam followers being in contact with the cam surface, such that when the shaft rotates, the cam surface peak and valley forces the arms and therefore the saw blades to reciprocate 180 degrees out of phase with each other.

11. The apparatus according to claim 10, further comprising a thin, friction-reducing insert separating each arm from the chassis and upon which each of the arms slide.

12. The apparatus according to claim 10, further comprising a thin, friction-reducing shell separating the arms and the chassis from the outer housing, each of the arms smoothly reciprocating between the shell and the chassis.

13. The apparatus according to claim 10, further comprising:
    a thin, friction-reducing insert separating each arm from the chassis and upon which each of the arms slide; and
    a thin, friction-reducing shell separating the arms and the chassis from the outer housing, each of the arms smoothly reciprocating between the shell and the chassis.

14. The apparatus according to claim 10 wherein the mounting means is adapted to position the saw blades in sliding contact with each other.

15. The apparatus according to claim 10, wherein each of the mounting means comprises:
    an axial slot on a lower end of each arm for receiving a saw blade; and
    a spring-loaded locking tab that locates in a transverse slot on the lower end of each arm, the tab adapted to engage a notch in the saw blade for securing the saw blade to the arm.

16. The apparatus according to claim 10 wherein the arms are mounted opposite of one another along a periphery of the body, parallel to the shaft, and free of contact from the cam.

17. A surgical instrument for sawing comprising:
    an outer housing;
    a chassis with a longitudinal axis and mounted in the outer housing;
    a rotatably-driven shaft having a rotational axis and located in the chassis;

a pair of arms mounted to the chassis for axial reciprocal movement relative to the chassis;

mounting means on a lower end of each of the arms for mounting a saw blade thereto for motion therewith;

a cylindrical cam having two sides with an annular cam surface on each of the sides, the cam being mounted on the shaft for rotation therewith, the cam having a thickness measured from one of the sides to the other; and two sets of cam followers, each of the sets comprising two of the cam followers, each cam follower having a rotational axis, each set rotatably mounted on an inner surface of the arms so that the axes of the cam followers are perpendicular to the axis of the shaft, the cam followers of each set being spaced apart by a dimension approximately equal to the thickness of the cam and positioned so that the cam surfaces are located between and in contact with the two cam followers in each of the sets, each of the cam surfaces having a peak and a valley 180 degrees apart such that when the shaft rotates, the cam forces the arms to reciprocate 180 degrees out of phase with each other.

18. The apparatus according to claim 17, further comprising a thin, friction-reducing insert separating each arm from the chassis and upon which each of the arms slide.

19. The apparatus according to claim 17, further comprising a thin, friction-reducing shell separating the arms and the chassis from the outer housing, each of the arms smoothly reciprocating between the shell and the chassis.

20. The apparatus according to claim 17, further comprising:

a thin, friction-reducing insert separating each arm from the chassis and upon which each of the arms slide; and a thin, friction-reducing shell separating the arms and the chassis from the outer housing, each of the arms smoothly reciprocating between the shell and the chassis.

21. The apparatus according to claim 17 wherein the mounting means is adapted to position the saw blades in sliding contact with each other.

22. The apparatus according to claim 17, wherein each of the mounting means comprises:

an axial slot on a lower end of each arm for receiving a saw blade; and a spring-loaded locking tab that locates in a transverse slot on the lower end of each arm, the tab adapted to engage a notch in the saw blade for securing the saw blade to the arm.

* * * * *